United States Patent [19]
Simons et al.

[11] Patent Number: 6,103,486
[45] Date of Patent: *Aug. 15, 2000

[54] PROCESS AND TEST KIT FOR DETERMINING FREE ACTIVE COMPOUNDS IN BIOLOGICAL FLUIDS

[75] Inventors: Guido Simons, Ingelheim am Rhein; Helmut Strecker, deceased, late of Pfungstadt, by Renate Strecker, née Weihrauch, legal heir; Peter Molz, Mainz; Gerd Schnorr, Bad Vilbel; Heinz Jürgen Skrzipczyk; Hans Wissmann, both of Bad Soden am Taunus, all of Germany

[73] Assignee: Dade Behring Marburg GmbH, Marburg, Germany

[*] Notice: This patent is subject to a terminal disclaimer.

[21] Appl. No.: 08/075,832

[22] Filed: Jun. 14, 1993

Related U.S. Application Data

[62] Division of application No. 07/884,874, May 18, 1992, Pat. No. 5,714,336, which is a continuation of application No. 07/697,494, May 3, 1991, which is a continuation of application No. 07/488,503, Mar. 5, 1990, which is a continuation of application No. 07/081,185, Aug. 4, 1987.

[30] Foreign Application Priority Data

Aug. 5, 1986 [DE] Germany .............................. 36 26 468

[51] Int. Cl.[7] .................................................. G01N 33/536
[52] U.S. Cl. .......................................... 435/7.93; 436/500
[58] Field of Search .................... 435/7.1, 7.93; 436/500, 501

[56] References Cited

U.S. PATENT DOCUMENTS

| | | | |
|---|---|---|---|
| 3,928,553 | 12/1975 | Hollander | 436/500 |
| 4,292,296 | 9/1981 | Parsons, Jr. | 424/1 |
| 4,366,143 | 12/1982 | Midgley et al. | 436/501 |
| 4,391,795 | 7/1983 | Pearlman | 436/500 |
| 4,426,453 | 1/1984 | Cree et al. | 436/500 |
| 4,711,855 | 12/1987 | Feinberg | 436/500 |

FOREIGN PATENT DOCUMENTS

| | | |
|---|---|---|
| 0106615 | 4/1984 | European Pat. Off. . |
| 0026103 | 4/1985 | European Pat. Off. . |
| 0155104 | 9/1985 | European Pat. Off. . |
| 29 36 307 | 4/1980 | Germany . |
| 34 15 818 | 4/1985 | Germany . |
| 36 00 365 | 7/1987 | Germany . |
| 2030290 | 4/1980 | United Kingdom . |
| 8401031 | 3/1984 | WIPO ............................. G01N 33/54 |
| WO 85/00226 | 1/1985 | WIPO . |

OTHER PUBLICATIONS

Tabachnick et al., "Thyroxing–Protein Interactions . . . ," Biochim Biophys Acta 537:169–175 (1978).
Wiersinga et al., "Radiommunoassays of Thyroxing . . . ," in *Methods in Enzymology* 84:272–302 (1982).
Eisen, "Antibody–Antigen Interactions," In Davis et al., Microbiology, Harper & Row, NY, pp. 326–328, 1980.

*Primary Examiner*—Donna C. Wortman
*Attorney, Agent, or Firm*—Finnegan, Henderson, Farabow, Garrett & Dunner, L.L.P.

[57] ABSTRACT

A method for determining the concentration of the free fraction of an active compound, present in a biological fluid, in the presence of natural binders, the free and bound fractions of the active compound being in mutual equilibrium, by a) contacting a sample of the fluid with an unlabeled antibody, b) separating the sample from the unlabeled antibody, c) incubating the unlabeled antibody with a labeled substance (tracer) for cross-reaction with the antibody and d) measuring the amount of the tracer which is or is not bound to the antibody and calculating from this the concentration of the free fraction of the active compound, wherein the quantity of the unlabeled antibody and/or its affinity for the active compound are so small that they do not substantially effect the equilibrium between the free and bound fractions of the active compound, and the affinity of the tracer for the antibody is substantially higher or substantially lower than that of the active compound itself, and a test kit suitable for this method.

8 Claims, 4 Drawing Sheets

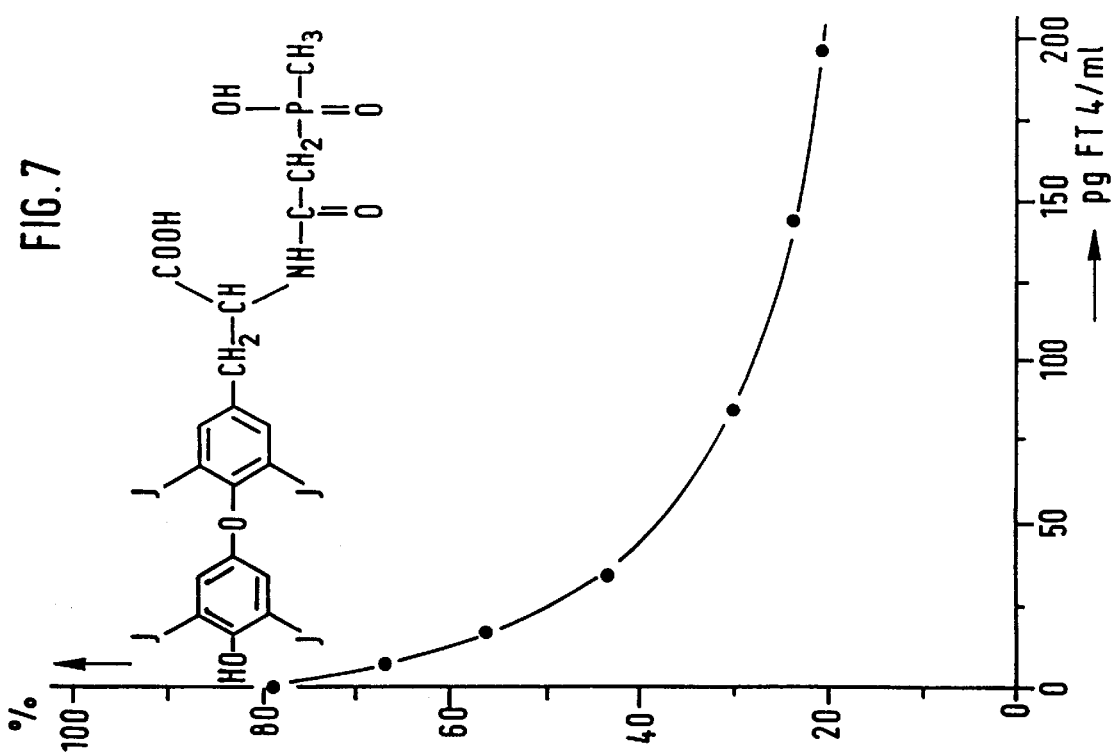

PROCESS AND TEST KIT FOR DETERMINING FREE ACTIVE COMPOUNDS IN BIOLOGICAL FLUIDS

This is a divisional of application Ser. No. 07/884,874 filed on May 18, 1992, now U.S. Pat. No. 5,714,336, which is a continuation application of Ser. No. 07/697,494 filed on May 3, 1991, abandoned, which is a continuation application of Ser. No. 07/488,503 filed on Mar. 5, 1990, abandoned, which is a continuation application of Ser. No. 07/081,185 as filed on Aug. 4, 1987 abandoned.

The invention relates to a method and a test kit for determining the concentration of the free fraction of an active compound, present in a biological fluid, in the presence of natural binders such as proteins, the free and bound fractions of the active compound being in mutual equilibrium.

It is known that most physiologically active substances are present in biological fluids such as blood partly in the free form and partly also bound to proteins such as globulins or albumins. The free and bound forms of the active compound are then in mutual equilibrium.

It is currently assumed that only that fraction of the active compound deploys physiological effects which is not bound to proteins. The reason is that, due to the binding to proteins, the active compound loses the ability to react with its specific receptor, which is a pre-condition for its activity. It has also been possible to show that certain medicaments lose their activity when they are bound to albumins in the serum, whereas their activity is enhanced by the addition of substances which displace them from the albumin bond. For this reason, a number of diagnostic methods have already been developed, by means of which only that fraction of an active compound which is not bound to proteins can be determined.

Thus, European Patent 26,103 has disclosed a method for determining the concentration of the free fraction of an active compound, present in a biological fluid, wherein the sample to be examined is mixed with a labeled derivative of the active compound and with a specific binder for the active compound and, after conversion of these reagents, that quantity of the labeled derivative of the active compound is measured which is or is not bound to the specific binder. The concentration of the free active compound in the biological fluid can then be calculated from this result. However, reliable measured results can be obtained by this method only if the labeled derivative of the active compound is selected such that it is bound almost exclusively to the specific binder but not to the natural binding proteins which are present in the biological fluid. However, this requirement cannot be satisfactorily met in many cases in practice.

For this reason, it has also already been proposed, in European Patent Application 155,104, to add to the sample of the biological fluid to be examined, apart from the labeled derivative of the active compound and the specific binder, a further substance which is intended to block the binding of the labeled derivative of the active compound to the natural proteins, as a result of this substance itself occupying the binding sites of the protein. This method is also described in German Patent 3,415,818.

International Patent Application WO 85/00,226 also attempts to solve the problem of binding the labeled active compound derivative to the natural proteins and the measuring errors thus caused. In this case, it is proposed to add a specific binder for the free active compound, a labeled derivative of the active compound and in addition also a special binder for the labeled active compound derivative to the biological fluid containing the free active compound. The labeled active compound derivative (tracer) will then react both with the specific binder for the active compound itself and with the binder for the active compound derivative, but not with the binding proteins, because the affinity of the latter for the tracer is much lower than that of the specific binder for the tracer.

The publications mentioned above show that the undesired binder of the tracer to natural proteins leads to a serious impairment of the measurement accuracy in the determination of the free fraction of an active compound in a biological fluid and that there is a need for solving this problem in the simplest way possible. It is therefore the object of the present invention to solve this problem without additional use of an agent which blocks the binding sites of the natural proteins, and even without the addition of a specific binder for the tracer.

BRIEF DESCRIPTION OF THE DRAWINGS

FIG. 7 illustrates the determination of free thyroxine by the method according to the invention using N-(methylphosphinoacetyl)-3,3',5,5'-tetraiodothyrosine as the tracer; and FIG. 8 illustrates the determination of free thyroxine by the method according to the invention using N-(ξ-aminocaproyl)-3,3',5,5'-tetraiodothyrosine as the tracer.

Figure 2:
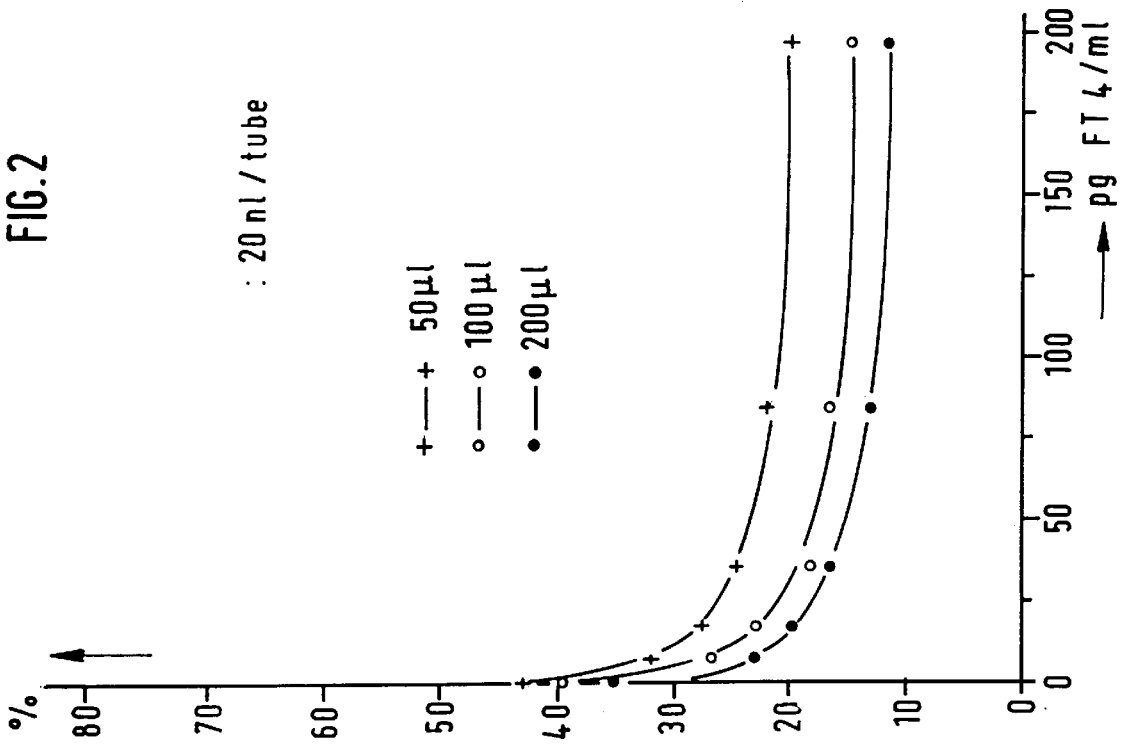
FIG. 2 illustrates the effect of varying the sample volume on the determination in FIG. 1.

It has now been found that the concentration of the free fraction of an active compound, present in a biological fluid, in the presence of natural binders, the free and bound fractions of the active compound being in mutual equilibrium, can be determined accurately by a) contacting a sample of the fluid with an unlabeled antibody, b) separating the sample from the unlabeled antibody, c) incubating the unlabeled antibody with a labeled substance (tracer) for cross-reaction with the antibody and d) measuring the amount of the tracer which is or is not bound to the antibody and calculating from this the concentration of the free fraction of the active compound, if the quantity of the unlabeled antibody and/or its affinity for the active compound are so small that they do not substantially affect the equilibrium between the free and bound fractions of the active compound, and the affinity of the tracer for the antibody is substantially higher or substantially lower than that of the active compound itself.

This method is particularly suitable for determining the free fraction of thyroxine, triiodothyronine and steroid hormones in biological fluids.

The method according to the invention differs from the determination methods described in the abovementioned publications in the first place by the fact that the sample of the biological fluid which is to be examined is separated off after the reaction with the unlabeled antibody. In this way, the interfering natural binding proteins are removed and can no longer interfere with the further course of the determination method and also can not cause any measurement inaccuracy.

Such a two-stage method is known per se from German Offenlegungsschrift 2,936,307. The latter likewise describes a method for determining the free fraction of an active compound by contacting the fluid sample, which is to be examined, with an unlabeled receptor, in order to bind the free active compound to the receptor. The fluid sample is then removed and the unlabeled receptor is incubated with a labeled active compound derivative and the quantity of the labeled reagent which is or is not bound to the receptor is then measured. However, this method has the great disadvantage that such large quantities of unlabeled receptor are used in the first stage that in fact all the free active compound is bound. Since, however, the free active compound and the active compound bound to proteins are in mutual equilibrium, the equilibrium is distributed by the binding of the free active compound to the receptor and active compound is traditionally liberated from its form bound to proteins. As a result, the concentrations of free active compound measured by this method are too high.

It is therefore a feature of the present invention that the unlabeled antibody is employed in such a small quantity that it cannot noticeably influence the equilibrium between the free active compound and that bound to protein. For the same reason, the affinity of the unlabeled antibody for the active compound may be only low. The intention is that neither the total free active compound should be bound to the unlabeled antibody nor should all the free binding sites of the unlabeled antibody be occupied.

An unlabeled antibody suitable for the determination method is appropriately selected from the group comprising the polyclonal or monoclonal antibodies, and its affinity for the active compound is determined in a few preliminary routine tests. After the fluid sample to be examined has been separated from the unlabeled antibody, the latter is then incubated with a labeled substance (tracer) for cross-reaction with the antibody. The tracer is labeled either with a radioactive atom such as iodine 125 or with a fluorescing or chemiluminescent compound. Labeling with an enzyme or a photochromophore is also possible.

An important point is that the tracer has a molecular structure which differs from that of the active compound which is to be determined. If, for example, thyroxine labeled with iodine 125 were employed as the tracer in the determination of thyroxine by the method according to the invention, the very flat standard curve drawn in FIG. 1 would be obtained, which would no longer allow unambiguous measured results to be read off. The curve shows the measured values which were obtained after incubation of a serum sample of rising free thyroxine content with a thyroxine antibody, separation of the serum sample and a second incubation period of 1 hour in the presence of $^{125}$iodo-thyroxine as the tracer.

As FIG. 2 shows, this unsatisfactory shape of the standard curve also cannot be improved by varying the sample volume under otherwise the same measurement conditions. The standard curves recorded with 50 $\mu$l, 100 $\mu$l and 200 $\mu$l show an unduly shallow shape in the ranges important for the measurement.

Figure 3:
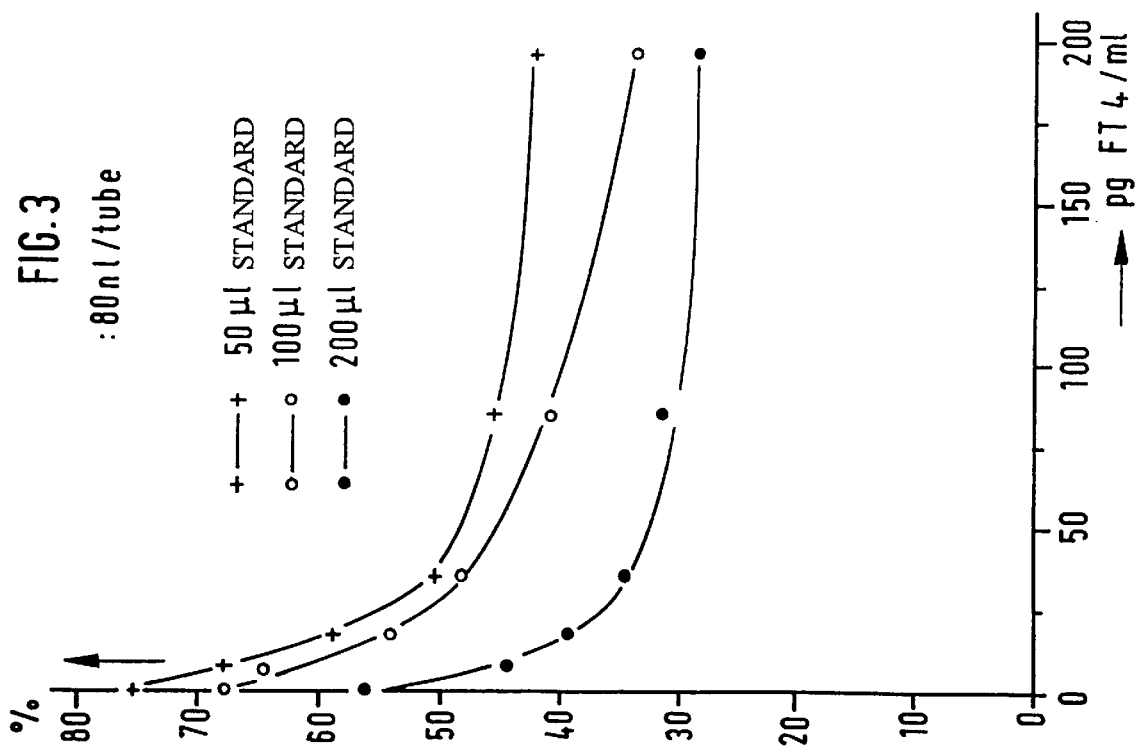
FIG. 3 illustrates the effect of decreasing the quantity of antibody to 80 nl per test on the determination in FIG. 1.

Whereas an antibody concentration of 20 nl was applied to the inner surface of a small test tube in the measurement shown in FIG. 2, FIG. 3 shows the same experiment with the quantity of antibody decreased to 80 nl per test. Even this does not lead to a steeper shape of the curve in a range important for the measurement.

Figure 1:
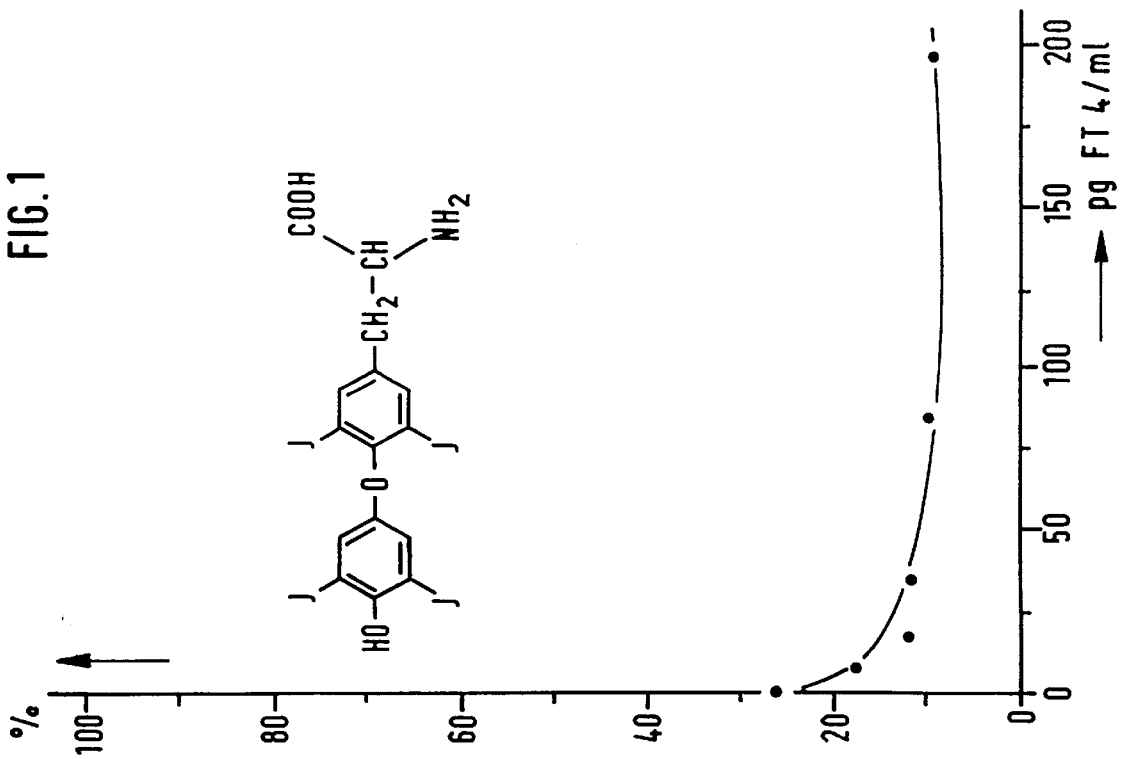
FIG. 1 illustrates the determination of free thyroxine by the method according to the invention, using thyroxine labelled with iodine 125 as the tracer.
Figure 4:
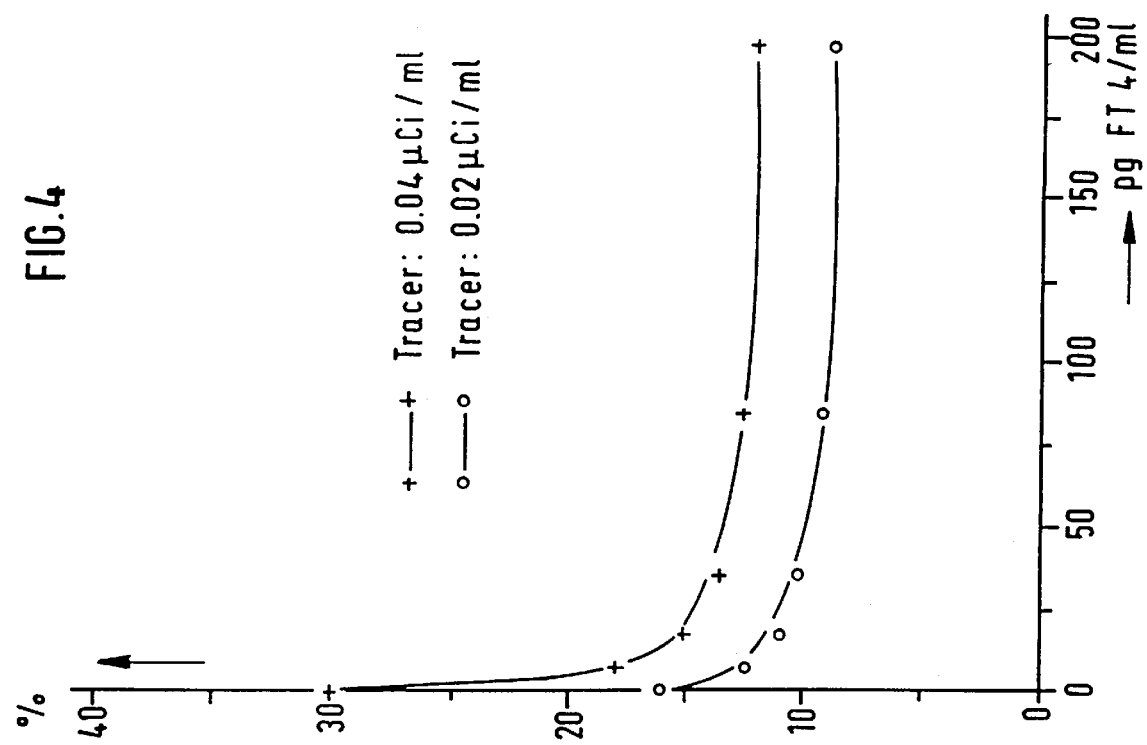
FIG. 4 illustrates the effect of the use of two tracers of different radioactivity on the determination in FIG. 1.

FIG. 4 shows the measured values which were obtained in a repeat of the measurements shown in FIG. 1 with the use of tracers of different radioactivity. The tracer activities were 0.04 $\mu$Ci and 0.02 $\mu$Ci. This did not provide more meaningful standard curves.

If, however, a thyroxine derivative which has been modified at the amino group, and the carboxyl group or at another site in the molecule is used for the determination of thyroxine by the method according to the invention, standard curves such as are shown in FIGS. 5 to 8 are obtained, wherein a defined thyroxine concentration can be unambiguously allocated to every tracer quantity bound to the antibody. Suitable tracers for the determination of thyroxine and triiodothyronine, which can be employed in the method according to the invention, have been described in German Patent Application P 36 00 365.4.

Due to its modified chemical structure, the affinity of the tracer for the antibody is higher or lower than that of the active compound itself. In general, it is advantageous to choose a tracer of which the affinity for the antibody is higher than that of the active compound itself. If, however, the concentration of the free active compound to be determined is very low, a tracer having a substantially lower affinity for the antibody than that of the active compound is preferable. This is because only a few binding sites of the antibody are occupied by the active compound present in a very low concentration, which would be hardly detectable if a tracer with a high affinity were then added. This might then create the impression as though no free active compound at all were present. By contrast, the satisfactory measured result is then still obtainable whenever a tracer of lower affinity is used.

In principal, all those substances can be employed as the tracer, the affinity of which for the antibody differs from that of the active compound which is to be determined, but compete with the active compound for the free binding sites of the antibody in a cross-reaction. For this reason, anti-idiotype antibodies, which are bound to the antibody used in the method according to the invention, can also be employed as the antibody. An assay based on this principal is described in European Patent Application 106,615.

It is thus a distinctive feature of the two-stage method according to the invention that the affinities of the active compound to be determined and of the tracer for the antibody differ. By contrast, the distinctive feature of the single-stage determination methods, such as are known, for example, from European Patent 26,103, is that the active compound to be determined and the tracer have different affinities for the binding proteins.

A determination method is thus made available which avoids the potential errors which are inherent in all single-stage methods for determining the free fraction of an active compound in a biological fluid, because of the presence of natural binding proteins. It is therefore distinguished by very precise measured values and manages with only two reagents.

A test kit suitable for carrying out the determination method according to the invention thus comprises an unlabeled antibody which reacts with the active compound to be determined and the quantity and/or affinity of which for the active compound are so small that it does not substantially affect the equilibrium between the free and bound fractions of the active compounds, and additionally a tracer, of which the affinity for the antibody is substantially higher or lower than that of the active compound itself. Such a test kit can be assembled in such a way that it allows the determination of the free fraction of any desired hormone, steroid, medicament, medicament metabolite, polypeptide, vitamin, tumor antigen, toxin or alkaloid. The determination of the free fraction of thyroxine, triiodothyronine and a steroid hormone is particularly preferred.

The following compounds have proven to be particularly suitable tracer compounds for the quantitative detection of thyroxine in biological fluids by the method according to the invention:

(1) 3,3',5,5'-tetraiodothyroacetic acid (FIG. 5), (2) 3,5-diiodo-4-(3,5-diiodo-4-oxyphenyl)-benzenesulfonic acid (FIG. 6), (3) N-(methylphosphinoacetyl)-3,3',5,5'-tetraiodothyrosine (FIG. 7) and (4) N-(ξ-aminocaproyl)-3,3',5,5'-tetraiodothyrosine (FIG. 8).

General Instructions for the Determination of Free Thyroxine by the Method According to the Invention 200 µl of a standard series (human series of increasing free thyroxine content) and 1000 µl of buffer are contacted for half an hour, with shaking, in small tubes which are coated with T4 antibody (20 ng of antibody per tube).

After the reaction solution has been poured out, 1000 µl of tracer (activity about 60,000 pulses per minute) are put into the pre-incubated tube. The mixture is incubated for one hour, and the unbound tracer is separated off and measured in a γ-counter.

Figure 5:
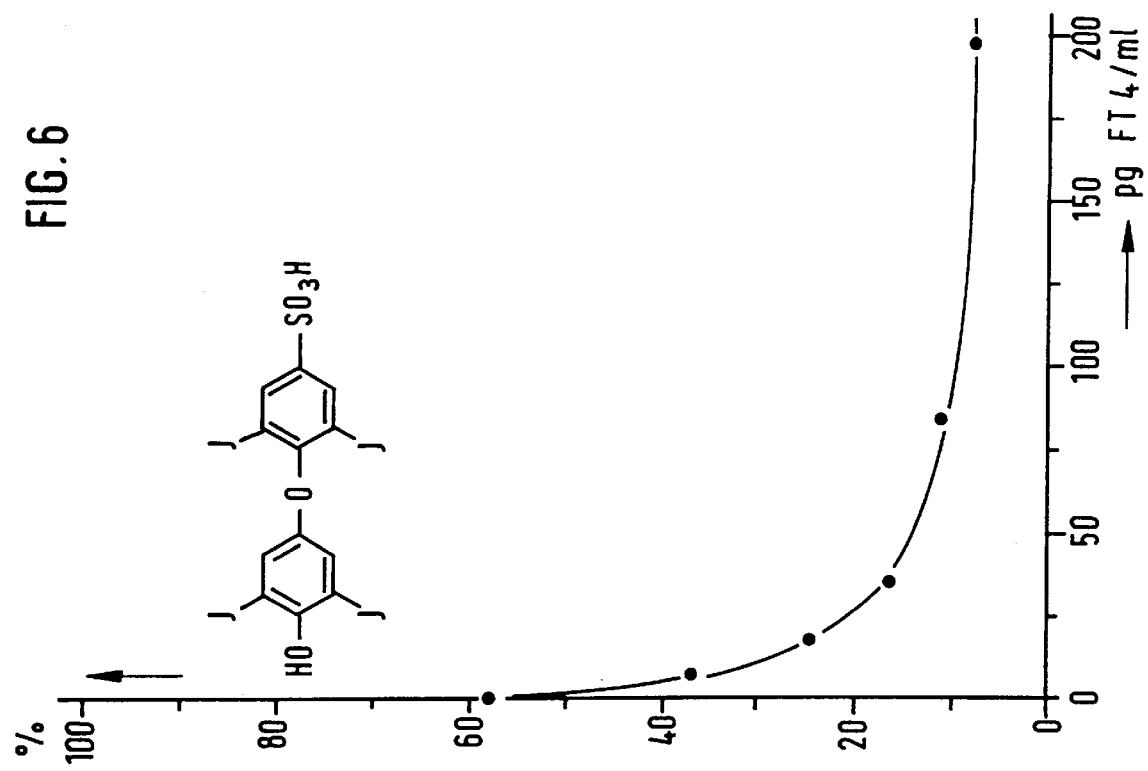
FIG. 5 illustrates the determination of free thyroxine by the method according to the invention using 3,3',5,5'-tetraiodothyroacetic acid as the tracer.
Figure 6:
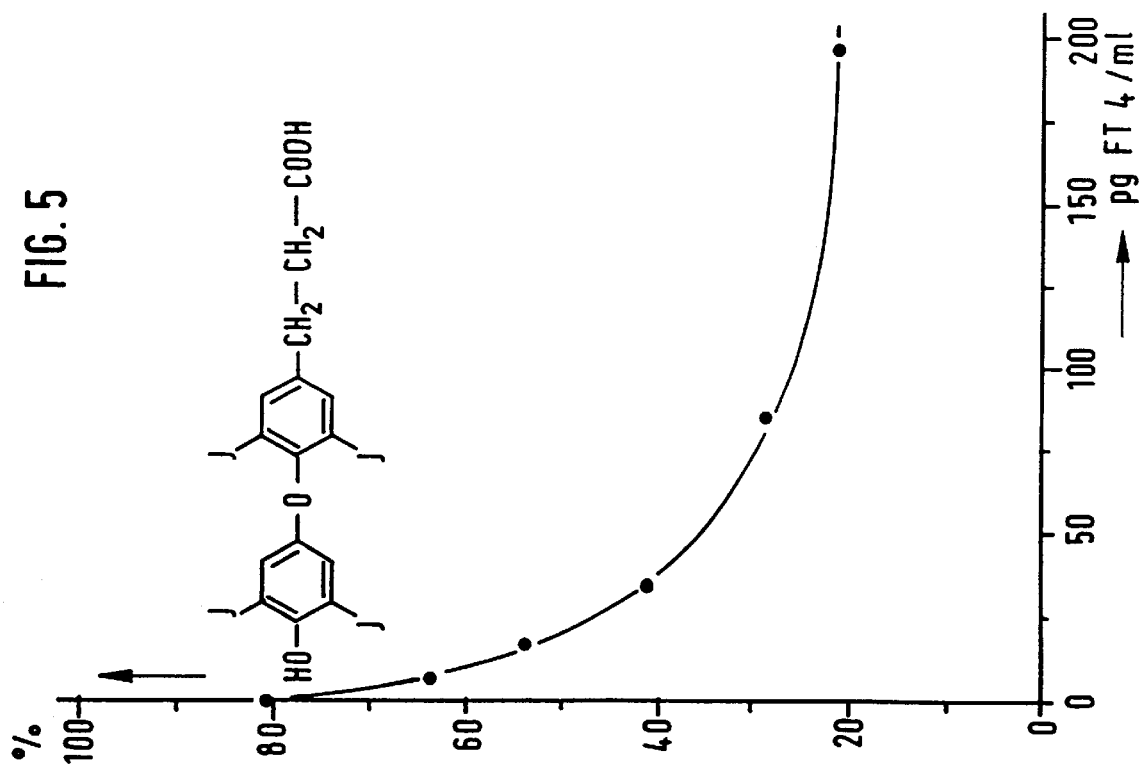
FIG. 6 illustrates the determination of free thyroxine by the method according to the invention using 3,5-diiodo-4-(3,5-diiodo-4-oxyphenyl)-benzenesulfonic acid as the tracer.

The results are shown in FIGS. 5 and 8.

What is claimed is:

1. A method for determining the concentration of the free fraction of triiodothyronine present in a biological fluid containing natural binders, with said free fraction and the bound fraction of triiodothyronine being in equilibrium, comprising the steps of:

(a) contacting a sample of said biological fluid with an unlabeled antibody to produce a reacted unlabeled antibody, with the quantity of said unlabeled antibody and the affinity of said unlabeled antibody for said free fraction of said triiodothyronine selected such that said unlabeled antibody does not substantially affect said equilibrium between said free fraction and said bound fraction of said triiodothyronine;

(b) separating said sample from said reacted unlabeled antibody of step (a);

(c) incubating said reacted unlabeled antibody of step (b) with a labeled tracer substance for cross-reaction with said unlabeled antibody, with the affinity of said tracer for said unlabeled antibody being substantially higher than or substantially lower than the affinity of said labeled antibody for said free fraction of said triiodothyronine, said tracer having a molecular structure which differs from that of the triiodothyronine to be determined and which structural difference has not been brought about by the labeling; and, (d) measuring the amount of said tracer which is or is not bound to said unlabeled antibody and calculating from said tracer amount the concentration of said free fraction of said triiodothyronine.

2. The method of claim 1 wherein said affinity of said tracer for said unlabeled antibody is substantially higher than said affinity of said unlabeled antibody for said free fraction of triiodothyronine.

3. The method of claim 1 wherein said affinity of said tracer for said unlabeled antibody is substantially lower than said affinity of said unlabeled antibody for said free fraction of triiodothyronine.

4. The method of claim 1, wherein said unlabeled antibody is a polyclonal or monoclonal antibody.

5. The method of claim 1, wherein said tracer is labeled with an entity selected from the group consisting of radioactive atom, a fluorescing group, a chemiluminescent group, an enzyme, and a photochromophor.

6. The method of claim 5 wherein said method is used for determining the free fraction of triiodothyronine, and wherein said tracer is a triiodothyronine which has been modified at the amino group, at the carboxyl group or at another site in the molecule.

7. The method of claim 5 wherein said tracer is labeled with iodine 125.

8. The method of claim 1 wherein the tracer is selected from the group consisting of 3,3',5,5'-tetraiodothyroacetic acid; 3,5-diiodo-4-(3,5-diiodo-4-oxyphenyl)-benzenesulfonic acid; N-(methylphosphinoacetyl)-3,3',5,5'-tetraiodothyrosine; and N-(ξ-aminocaprol)-3,3',5,5'-tetraiodothyrosine.

* * * * *